(12) United States Patent
Ladet et al.

(10) Patent No.: US 10,253,152 B2
(45) Date of Patent: Apr. 9, 2019

(54) PROCESS FOR PREPARING A POROUS LAYER

(71) Applicant: Sofradim Production, Trévoux (FR)

(72) Inventors: Sébastien Ladet, Caluire & Cuire (FR); Nicolas Prost, Orlienas (FR)

(73) Assignee: Sofradim Production, Trévoux (FR)

( * ) Notice: Subject to any disclaimer, the term of this patent is extended or adjusted under 35 U.S.C. 154(b) by 616 days.

(21) Appl. No.: 14/423,150

(22) PCT Filed: Sep. 26, 2013

(86) PCT No.: PCT/EP2013/070070
§ 371 (c)(1),
(2) Date: Feb. 23, 2015

(87) PCT Pub. No.: WO2014/049055
PCT Pub. Date: Apr. 3, 2014

(65) Prior Publication Data
US 2015/0240046 A1   Aug. 27, 2015

(30) Foreign Application Priority Data

Sep. 27, 2012 (FR) ..................... 12 59084

(51) Int. Cl.
*B05B 3/00* (2006.01)
*C08J 9/28* (2006.01)
(Continued)

(52) U.S. Cl.
CPC ............... *C08J 9/28* (2013.01); *A61L 27/20* (2013.01); *A61L 31/042* (2013.01);
(Continued)

(58) Field of Classification Search
CPC ..... C08J 9/28; C08J 2201/048; A61L 31/048; A61L 31/042; A61L 31/146;
(Continued)

(56) References Cited

U.S. PATENT DOCUMENTS 4,034,032 A     7/1977  Hendricks
7,914,808 B2 *  3/2011  Malaviya ................ A61L 27/18
                                                        424/422

(Continued)

FOREIGN PATENT DOCUMENTS

WO    WO2010043978 A2 *  4/2010  ............. A61L 27/24

OTHER PUBLICATIONS

Albright, LF, Albright's Chemical Engineering Handbook, 2009, CRC Press, p. 591-608.*

(Continued)

*Primary Examiner* — William P Bell
*Assistant Examiner* — Andrew L Swanson

(57) ABSTRACT

The present invention relates to a process for preparing a porous layer of biocompatible polymer, having a uniform density and porosity, comprising the following steps:
  a) a quantity Qp of solution of the said polymer, having a viscosity Vp, is poured into a mold in order to form a first sublayer, the surface of the first sublayer being left to the open air;
  b) a quantity Qs of solvent, having a viscosity Vs, lower than Vp, is spread uniformly over the surface of the first sublayer so as to form a second sublayer;
  c) the first and second sublayers are subjected to a step of lyophilization, in which the said polymer is a polysaccharide chosen from hyaluronic acid, alginic acid and chitosan, salts thereof and mixtures thereof.

22 Claims, 2 Drawing Sheets

(51) Int. Cl.
*A61L 27/20* (2006.01)
*C08J 5/18* (2006.01)
*A61L 31/04* (2006.01)
*A61L 31/14* (2006.01)

(52) U.S. Cl.
CPC ............... *A61L 31/146* (2013.01); *C08J 5/18* (2013.01); *A61L 2400/18* (2013.01); *C08J 2201/048* (2013.01); *C08J 2207/10* (2013.01); *C08J 2305/04* (2013.01); *C08J 2305/08* (2013.01)

(58) Field of Classification Search
CPC ..... B29C 39/003; B29C 39/02; B29C 39/021; B29C 39/38; A61K 9/0085
See application file for complete search history.

(56) References Cited

U.S. PATENT DOCUMENTS 8,865,215 B2 * 10/2014 Ladet ..................... A61L 27/48
623/23.72
2008/0242850 A1 10/2008 Kim et al.
2012/0149659 A1 * 6/2012 Haggard ................ A61K 31/00
514/55

OTHER PUBLICATIONS

Kyung W. Kim et. al, Antimicrobial activity against foodborne pathogens of chitosan biopolymer films of different molecular weights, 2010, LWT—Food and Technology, p. 565.*
Nitar Nwe et. al, Selection of a biopolymer based on attachment, morphology and proliferation of fibroblast NIH/3T3 cells for development of a biodegradable tissue regeneration template: Alginate, bacterial cellulose, and gelatin, 2009, Process Biochemistry, 458.*
Caiqin Qin et. al, Water-solubility of Chitosan and its antimicrobial activity, Nov. 8, 2005, Carbohydrate Polymers, 63, p. 367, 370.*
"Viscosity". Oxford Dictionary (Online). Accessed on: Apr. 3, 2017.*
Tanny, G.B., The Surface Tension of Polymer Solutions and Asymmetric Membrane Formation, 1974, Journal of Applied Polymer Science, vol. 18, p. 2160.*
European Office Action dated Mar. 31, 2016 in corresponding European Patent Application No. 13774624.4, 4 pages.
International Search Report for PCT/EP13/070070 date of completion is Oct. 15, 2014 (3 pages).

* cited by examiner

PROCESS FOR PREPARING A POROUS LAYER

CROSS-REFERENCE TO RELATED APPLICATIONS

This application is a National Stage Application of PCT/EP13/070070 under 35USC § 371 (a), which claims priority of French Patent Application Serial No. 12/59084 filed Sep. 27, 2012, the disclosures of each of the above-identified applications are hereby incorporated by reference in their entirety.

BACKGROUND

1. Technical Field

The present invention relates to a process for preparing a homogeneous porous layer of biocompatible polymer, the said process comprising, inter alia, a step of lyophilization of a viscous solution or suspension of the said polymer.

2. Description of Related Art

A surgical implant for repairing the dura mater is often in the form of a relatively flat slab formed from a porous layer obtained from the lyophilization of a solution comprising biopolymers.

Such a surgical implant should have good conformability in order to be able to take on the exact shape of the dura mater. It should also have on its thickness the most uniform possible density and porosity in order to be efficient once implanted.

All the parameters that are liable to have an influence on the final homogeneity of a lyophilized product cannot be totally mastered and controlled in the course of a lyophilization process. Specifically, for example, the temperature in the product may vary according to the thickness of the product. Similarly, the nature of the mould initially receiving the viscous composition may also have an influence on the lyophilization kinetics. Similarly, the difference in temperature at the lower edge of the mould and on the upper face of the product, simply in contact with air, may also have consequences on the homogeneity of the lyophilized product.

In point of fact, it has been observed that many products, all in the form of a lyophilized layer, have a non-uniform density and porosity: in particular, the upper part of the lyophilized layer, that which is in contact with air during the lyophilization process, has a density that is much higher than the rest of the layer. On the other hand, this upper part has a much lower porosity than the rest of the layer. In certain cases, the porosity at the surface of the layer is nonexistent. Finally, in the case where surface porosity exists, the surface pores are not connected to the pores of the inner porosity of the layer.

Such a phenomenon affects the properties of the products obtained: in particular, the capacity of the product to absorb fluids rapidly is compromised. Consequently, the conformability of the product is degraded, and its handling is made more difficult. This represents major drawbacks when these products are implanted into the human body, for example in the form of surgical implants for the purpose of repairing a defect in the dura mater.

It would be desirable to perform a process for preparing porous layers which would avoid this phenomenon and which would make it possible to make implants, in particular for repairing the dura mater, obtained by lyophilization of viscous polymeric compositions, and having the most uniform possible density and porosity over the entire thickness of the layer, and in particular having a surface porosity in which the pores are connected to the pores of the inner porosity of the layer.

SUMMARY

The present invention relates to a process for preparing a homogeneous porous layer of biocompatible polymer, comprising the following steps:
a) a quantity $Q_p$ of solution or suspension of the said polymer, having a viscosity $V_p$, is poured into a mould in order to form a first sublayer, the surface of the first sublayer being left to the open air,
b) a quantity $Q_s$ of solvent, having a viscosity $V_s$, lower than $V_p$, is spread uniformly over the surface of the first sublayer so as to form a second sublayer,
c) the first and second sublayers are subjected to a step of freezing and then lyophilization.

The process according to the invention makes it possible to avoid the formation, in the resulting porous layer, of an upper part, and in particular of a surface, having an increased density and a reduced, or even nonexistent, porosity, relative to that of the rest of the said layer.

BRIEF DESCRIPTION OF THE DRAWINGS

The invention and the advantages thereof will emerge more clearly from the examples below and from the attached figures, in which.

DETAILED DESCRIPTION

Figure 1A:
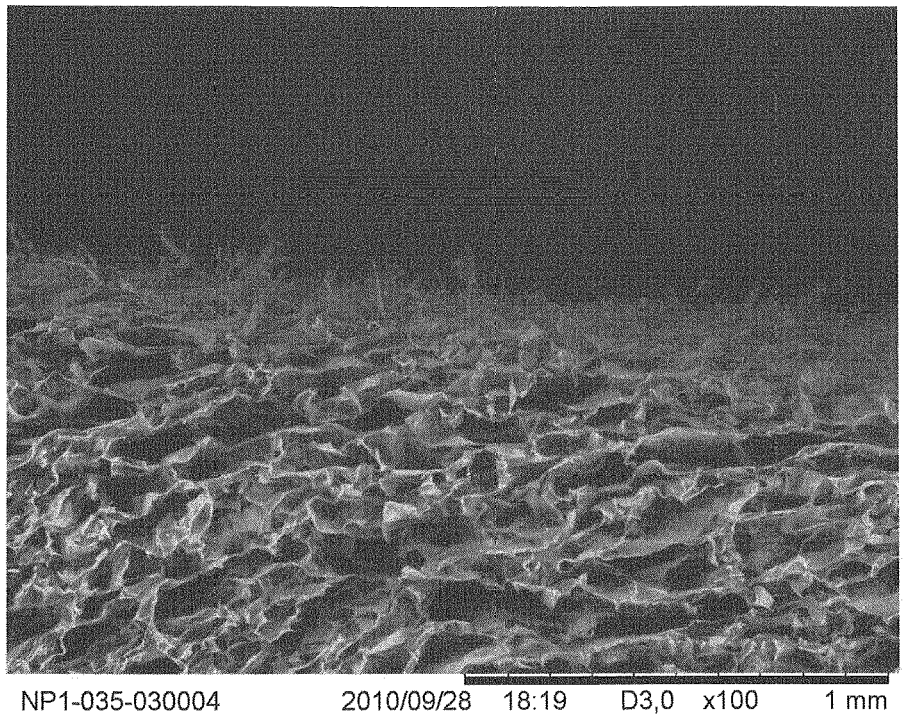
FIG. 1A is a scanning electron microscope (Hitachi) view at magnification ×100 of a section of the upper part of a porous layer obtained via the process according to the invention.

In the present patent application, the term "porous layer" means a layer bearing pores, or spaces, alveolae, holes or orifices, optionally uniformly distributed, not only at the surface but also within the thickness of the said layer, and more or less interconnected, according to the lyophilization process used. Such lyophilization processes are known. It is known practice to vary the temperature and rate of freezing and also the characteristics of the polymer solution or suspension to be lyophilized (pH, concentration, etc.) as a function of the structure of the sponge that it is desired to obtain (see U.S. Pat. No. 4,970,298; Doillon et al., J. Biomed. Mater Res., 1986; Schoof, J. Biomed. Mater Res., 2001; O'Brien et al., Biomaterials, 2004).

In the present patent application, the term "homogeneous porous layer" means a porous layer obtained by lyophilization, in which the upper part, and in particular the surface, has a porosity in which the pores are connected with the pores of the porosity of the inner structure of the said layer. The term "upper part and surface" of the porous layer obtained by lyophilization means the upper part and the surface in contact with air during the lyophilization process.

The porous layer obtained via the process of the invention has a uniform porosity, which, in particular, is present throughout its thickness. The upper part of the porous layer obtained via the process of the invention, i.e. the part of the first sublayer and the second sublayer located in the region of the open air during the lyophilization process, remains porous despite the lyophilization process. In particular, the pores of the surface of this upper part are connected with the pores of the core of the layer. Such a homogeneous porous layer may thus be used for the manufacture of surgical implants for repairing the dura mater. Specifically, due to its uniform porosity present throughout its thickness, the porous layer obtained via the process according to the invention conserves good conformability, a good capacity for absorbing fluids, such as biological fluids, in particular cerebrospinal fluid during implantation, irrespective of its surface placed in contact with such fluids.

In the present patent application, the surface porosity of a layer is measured according to the following method: samples of the layer are observed with a scanning electron microscope without a preliminary metallization step. The images are then analysed using the Nikon NIS-D v3.0 (ECME 502) software so as to evaluate the porosity of the layer. According to the present method, ten measurements are taken on the surface of the layer using circular modelling of the size of the pores. The mean and standard deviation of the pore size, measured by means of the diameter of these pores, are then calculated on the ten pore size measurements taken.

In a first step of the process according to the invention, a quantity $Q_p$ of solution or suspension of a biocompatible polymer, having a viscosity $V_p$, is poured into a mould so as to form a first sublayer, the surface of the first sublayer being left in the open air.

As biocompatible polymer that may be used in the present invention, mention may be made of any biocompatible polymer that is soluble in an aqueous formulation, requiring a hot or cold solubilization step, and which may contain salts, acids or bases.

In one embodiment, the polymer is a polysaccharide.

The polysaccharides may be chosen from hyaluronic acid, alginic acid, polyglucuronic acid, chitosan, starch, agar-agar, guar, soluble cellulose derivatives, salts thereof and mixtures thereof. The said polysaccharide may be crosslinked.

The polyglucuronic acid may be of bacterial origin, such as the polysaccharide secreted by the mutant strain of *Rhizobium meliloti* M5N1CS(NCIMB 40472), according to the teaching of patent WO 9318174, or alternatively it may be obtained by selective oxidation of the primary hydroxyls of cellulose.

The soluble cellulose derivatives may be chosen from cellulose ethers, such as carboxymethylcellulose, and oxidized celluloses, and mixtures thereof.

Preferably, the oxidized celluloses are chosen from oxidized cellulose in which the $C_6$ primary alcohol is partially or totally oxidized to carboxylic acid, for example to give polyglucuronic acid, the cellulose oxidized in the form of polyaldehydes with periodic acid, the cellulose of "viscose" type, manufactured from a solubilized and then regenerated and oxidized cellulose pulp, and mixtures thereof.

Several varieties of regenerated cellulose have been industrially developed. Mention may be made, for example, of the "viscose" process, which is based on the solubility of cellulose xanthate in a dilute sodium hydroxide solution. Mention may also be made of the "cupro-ammonium" process performed, for example, by the company Bemberg in Italy or the company Asahi Chemical Industries in Japan, and which consists in dissolving cellulose in an ammoniacal copper solution. Another process for preparing regenerated cellulose that is suitable for use in the present invention is the process of dissolving cellulose in organic phase with N-methylmorpholine oxide (NMMO), known as the "Lyocell® process", performed, for example, by the company Lenzing in Austria.

The said biocompatible polymer is a polysaccharide chosen from hyaluronic acid, alginic acid and chitosan, salts thereof and mixtures thereof. For example, the said polymer is chitosan. Chitosan makes it possible to give the final porous layer good mechanical properties. Moreover, chitosan is a biodegradable material whose biodegradation time varies as a function of the degree of acetylation of the said chitosan. Thus, depending on the degree of acetylation of the chitosan, it is possible to vary the degradation time of the porous layer obtained.

The biocompatible polymer is placed in solution or in suspension in an aqueous solution. The biocompatible polymer is generally dissolved in water with mechanical stirring. The temperature and pH of the solution may be adjusted so as to facilitate the dissolution of the polymer.

In the present patent application, the viscosity of a composition, and in particular the viscosity $V_p$ of the solution or suspension of biocompatible polymer and the viscosity $V_s$ of the solvent, are measured according to the following method: 5 ml of composition are placed in an RM200 (ECME 663) viscometer. The compositions are analysed according to the Casson and Bingham methods, at 25° C., for shear rate gradients D of between 300 and 800. The mean viscosity of the composition is determined on the plateau of the viscosity curve as a function of the shear.

A quantity $Q_p$, by weight, of the solution or suspension of biocompatible polymer thus prepared is poured into a mould formed from a material that is inert towards the said solution or suspension. A first sublayer is thus formed, the upper surface of which is left to the open air.

In a second step of the process according to the invention, a quantity $Q_s$ of solvent, having a viscosity $V_s$ below $V_p$, is spread uniformly over the surface of the first sublayer so as to form a second sublayer.

In one embodiment of the process of the invention, the solvent is chosen from water, alcohols such as methanol, ethanol, propanol, 1,2-propanediol and isopropanol, and mixtures thereof. The solvent may also comprise an acid so as to adjust its pH to the desired value.

In one embodiment, the solvent is water, for example supplemented with acetic acid to give the said solvent a pH below 7.

For example, in one embodiment of the process according to the invention, when the biocompatible polymer is chitosan, the solvent is preferably an aqueous solution of acetic acid, for example at pH 3.5. Surface precipitation of the chitosan at the time of application of the solvent to the first sublayer is thus avoided.

In one embodiment, the said first sublayer has a thickness $E_p$, and the said second sublayer has a thickness $E_s$, the ratio $E_s E_p$ ranging from 0.05 to 0.4 and preferably from 0.15 to 0.25.

Such a ratio makes it possible to obtain a porous layer after lyophilization, the porosity of which is homogeneous: in particular, the pores of the surface of the porous layer are connected to the pores of the inner structure of the said layer. Thus, in the final porous layer obtained, it is no longer possible to distinguish the initial separation of the two sublayers.

In one embodiment, the ratio VsVp ranges from 0.02 to 0.00001 and preferably from 0.01 to 0.0002.

Such a ratio makes it possible to obtain a porous layer after lyophilization, the porosity of which is homogeneous: in particular, the pores of the surface of the porous layer are connected to the pores of the inner structure of the said layer. Thus, in the final porous layer obtained, it is no longer possible to distinguish the initial separation of the two sublayers.

In a third step of the process according to the invention, the first and second sublayers are subjected to a step of freezing, followed by lyophilization.

The freezing and lyophilization steps are known to those skilled in the art and will not be described in detail herein.

The porous layer obtained has a surface porosity in which the pores are connected with the pores of the inner structure of the layer. The layer thus obtained has good conformability and a good capacity to absorb fluids, such as biological fluids.

EXAMPLE 1: (ACCORDING TO THE INVENTION)

121 g of a 1% (ww) of chitosan aqueous solution (degree of acetylation 30%) is prepared at pH=3.5 by adding acetic acid in stoichiometric proportions: the viscosity of this solution, measured as described in the present patent application, is 1196 mPa/s.

After removal of the air bubbles under vacuum, the viscous solution is poured into a rectangular mould 18 cm×13 cm in size. The thickness of the first sublayer thus obtained is about 5.2 mm.

23.3 g of an aqueous acetic acid solution at pH=3.5 are spread uniformly over the first sublayer so as to form a second sublayer about 1 mm thick. The viscosity of this aqueous acetic acid solution, measured as described in the present patent application, is 1 mPa/s.

The assembly formed by the first sublayer and the second sublayer is frozen and then lyophilized for about 24 hours, and then neutralized in a 0.5 M solution of NaOH in ethanol for 5 minutes. After washing with sterile water until a pH of 7 is obtained, the product obtained is again frozen and then lyophilized to produce a porous layer.

The surface porosity of the porous layer obtained is measured in the manner described in the present patent application: the values obtained for the ten measurements taken are collated in the following table:

| Sample | Measured pore diameter in mm |
|---|---|
| 1 | 0.1519 |
| 2 | 0.1428 |
| 3 | 0.1282 |
| 4 | 0.1058 |
| 5 | 0.1053 |
| 6 | 0.1052 |
| 7 | 0.1003 |
| 8 | 0.1003 |
| 9 | 0.0859 |
| 10 | 0.0843 |

Thus, the average of the pore diameters of the surface of the layer is 0.111 mm and the standard deviation is 0.02.

The porous layer obtained has a uniform porosity, in particular a porosity present throughout its thickness.

Figure 1B:
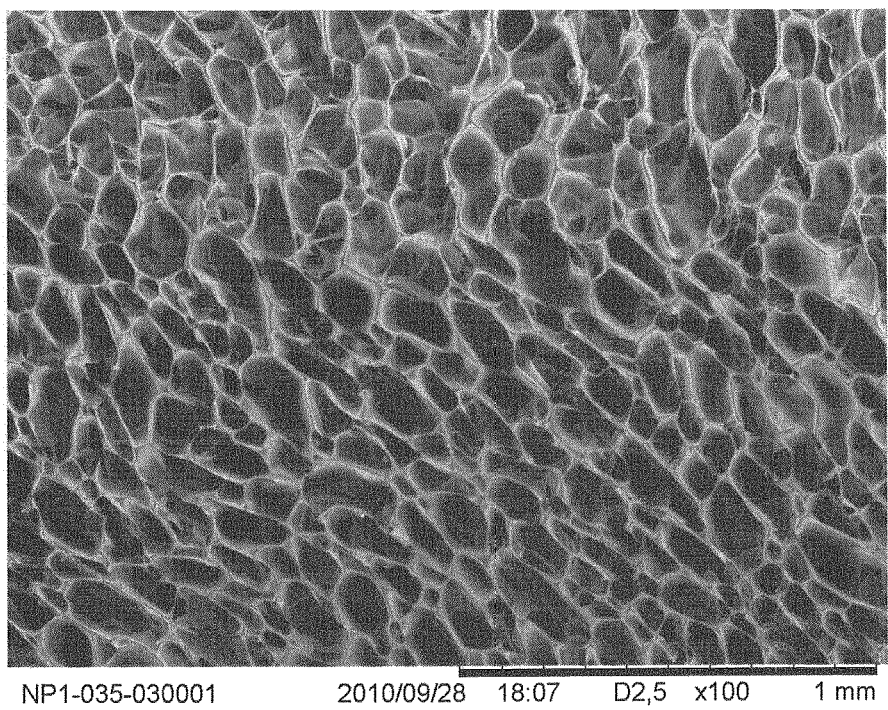
FIG. 1B is a scanning electron microscope (Hitachi) view at magnification ×100 of the surface of the said upper part of the porous layer of FIG. 1A.

These properties emerge clearly from FIGS. 1A and 1B, which are, respectively, scanning electron microscope (Hitachi) views at magnification ×100:

of a section of the upper part, i.e. that left to the open air during the process of freezing-lyophilization of the two sublayers, of the porous layer obtained in the present example, and of the surface of the same upper part of this porous layer.

It is observed that the pores are uniformly distributed in the upper part of the porous layer, and also at the surface of this upper part.

In particular, it is observed that the pores of the surface of the layer are totally connected to the pores of the inner structure of the layer: thus, a communication can be established between the pores of the surface and those of the core of the layer.

The porous layer obtained in the present example is particularly suitable for forming a surgical implant, for example an implant that is particularly effective for reinforcing the dura mater. Its properties of absorbing biological fluids are good, irrespective of the face of the implant considered. Moreover, this implant has good handleability and conformability.

EXAMPLE 2: (COMPARATIVE)

121 g of a 1% (ww) of chitosan aqueous solution (degree of acetylation 30%) is prepared at pH=3.5 by adding acetic acid in stoichiometric proportions: the viscosity of this solution, measured as described in the present patent application, is 1196 mPa/s.

After removing the air bubbles under vacuum, the viscous solution is poured into a rectangular mould 18 cm×13 cm in size. The thickness of the layer thus obtained is about 5.2 mm.

The layer obtained is frozen and then lyophilized for about 24 hours, and then neutralized in a 0.5 M solution of NaOH in ethanol for 5 minutes. After washing in sterile water until a pH of 7 is obtained, the product obtained is again frozen and then lyophilized to produce a layer, which is not porous at the surface.

Figure 2A:
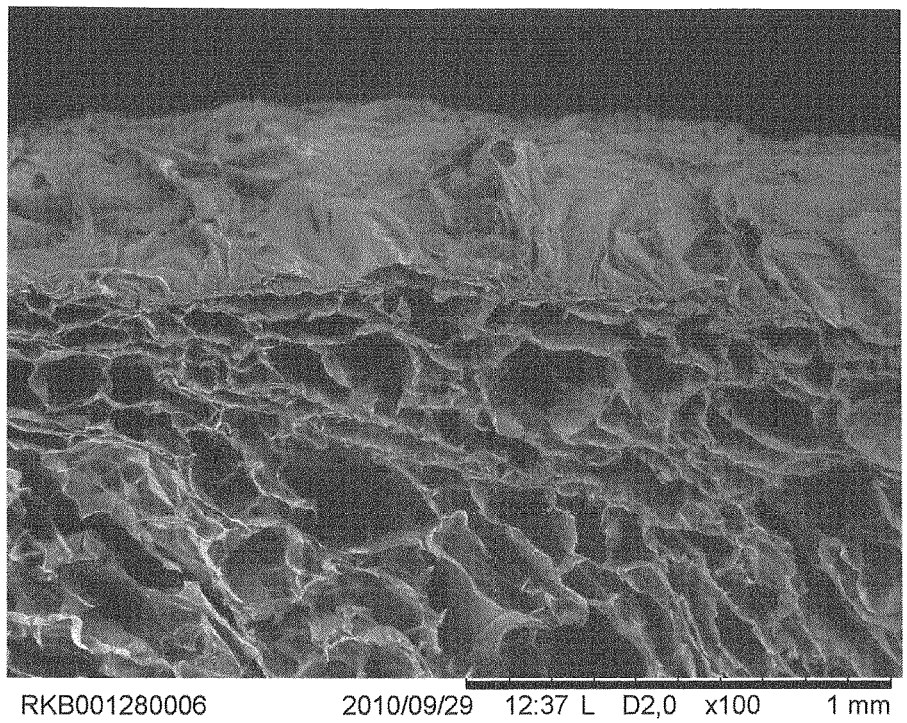
FIG. 2A is a scanning electron microscope (Hitachi) view at magnification ×100 of a section of the upper part of a porous layer obtained via a process of the prior art.
Figure 2B:
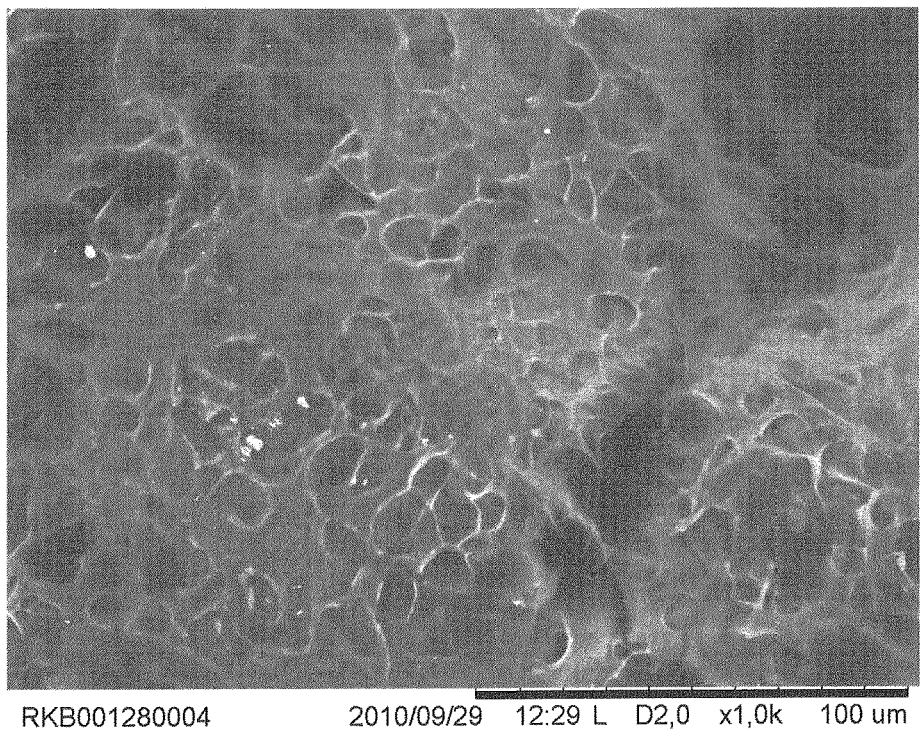
FIG. 2B is a scanning electron microscope (Hitachi) view at magnification ×100 of the surface of the said upper part of the porous layer of FIG. 2A.

FIGS. 2A and 2B are, respectively, scanning electron microscope (Hitachi) views at magnification ×100:

of a section of the upper part, i.e. that left to the open air during the process of lyophilization, of the layer obtained in the present example, and of the surface of the same upper part of this layer.

As emerges clearly from these views, the layer obtained is not porous at the surface.

The surface porosity of the layer obtained is nonexistent and could not be measured in the manner described in the present patent application.

Thus, it is clearly seen from FIG. 2B that the surface of the upper part of the layer obtained in the present example has few pores or voids: thus, the capacity for absorbing fluids of this layer is greatly impaired on the surface considered. This is likewise the case as regards the structure of the layer below this surface, in the upper part of the layer.

It is also seen from FIGS. 2A and 2B that the upper part of the layer obtained does not have pores connected with those of the inner structure of the layer.

Thus, the layer obtained in the present example has little conformability, absence of porosity of its upper part, and in particular of its surface, giving this layer a rigidity that is detrimental to its conformability.

What is claimed is:

1. A process for preparing a homogeneous porous layer of biocompatible polymer, comprising the following steps:
   a) pouring a quantity of a solution or suspension, having a first viscosity and including the biocompatible polymer, into a mold in order to form a first sublayer having a surface left to open air,
   b) spreading a quantity of a solvent, having a second viscosity lower than the first viscosity, uniformly over the surface of the first sublayer so as to form a second sublayer, wherein the solvent is free of the biocompatible polymer and spreading the solvent avoids surface precipitation of the biocompatible polymer,
   c) freezing and lyophilizing the first and second sublayers to form a homogenous porous layer, wherein the biocompatible polymer is a polysaccharide chosen from hyaluronic acid, alginic acid and chitosan, salts thereof and mixtures thereof.

2. The process according to claim 1, wherein the biocompatible polymer is chitosan.

3. The process according to claim 1, wherein the biocompatible polymer is hyaluronic acid.

4. The process according to claim 1, wherein the biocompatible polymer is alginic acid.

5. The process according to claim 1, wherein the solvent is chosen from water, an acid, alcohols and mixtures thereof.

6. The process according to claim 5, wherein the solvent is water.

7. The process according to claim 6, wherein the solvent further includes acetic acid.

8. The process according to claim 7, wherein the solvent has a pH below 7.

9. The process according to claim 7, wherein the solvent has a pH of 3.5.

10. The process according to claim 1, wherein the first sublayer has a first thickness, and the second sublayer has a second thickness, wherein a ratio of the second thickness/the first thickness ranges from 0.05 to 0.4.

11. The process according to claim 10, wherein the ratio of the second thickness/the first thickness ranges from 0.15 to 0.25.

12. The process according to claim 1, wherein a ratio of the second viscosity/the first viscosity ranges from 0.02 to 0.00001.

13. The process according to claim 1, wherein the ratio of the second viscosity/the first viscosity ranges from 0.01 to 0.0002.

14. The process according to claim 1, wherein the porous layer after lyophilizing includes surface pores which are connected to pores of an inner structure of the porous layer.

15. The process according to claim 1, wherein the first and second sublayers of the porous layer are no longer distinguishable after lyophilizing.

16. The process according to claim 1, wherein the solution or suspension consists essentially of the polysaccharide, the solvent, and optionally an acid.

17. The process according to claim 2, further comprising neutralizing the porous layer after freezing and lyophilizing.

18. A process for preparing a homogeneous porous layer of chitosan, comprising the following steps:
   a) pouring a quantity of an acidic chitosan solution, having a first viscosity, into a mold to form a first sublayer having a surface left to open air,
   b) spreading a quantity of an acid solution comprising acetic acid, having a second viscosity lower than the first viscosity, uniformly over the surface of the first sublayer so as to form a second sublayer, wherein the solvent is free of the chitosan and spreading the acid solution avoids surface precipitation of the chitosan,
   c) freezing and lyophilizing the first and second sublayers, wherein the porous layer includes a uniform porosity throughout.

19. The process according to claim 18, further comprising neutralizing the porous layer after freezing and lyophilizing.

20. The process according to claim 19, further comprising freezing and lyophilizing the porous layer after neutralizing.

21. The process according to claim 18, wherein the first sublayer has a first thickness, and the second sublayer has a second thickness, wherein a ratio of the second thickness/the first thickness ranges from 0.05 to 0.4 and a ratio of the second viscosity/the first viscosity ranges from 0.02 to 0.00001.

22. The process according to claim 18, wherein the acidic chitosan solution consists essentially of chitosan, a solvent, and optionally an acid.

* * * * *